United States Patent [19]

Emberger et al.

[11] Patent Number: 4,563,365
[45] Date of Patent: Jan. 7, 1986

[54] FLAVORING WITH 5-METHYL-HEPT-2-EN-4-ONE

[75] Inventors: Roland Emberger; Manfred Köpsel; Jürgen Brüning; Rudolf Hopp; Theodor Sand, all of Holzminden, Fed. Rep. of Germany

[73] Assignee: Haarmann & Reimer GmbH, Holzminden, Fed. Rep. of Germany

[21] Appl. No.: 679,180

[22] Filed: Dec. 7, 1984

[30] Foreign Application Priority Data

Dec. 17, 1983 [DE] Fed. Rep. of Germany ....... 3345784

[51] Int. Cl.$^4$ .............................................. A23L 1/226
[52] U.S. Cl. .................................. 426/534; 252/522 R
[58] Field of Search ......................................... 426/534

[56] References Cited

U.S. PATENT DOCUMENTS 4,315,911 2/1982 Boden ............................. 426/534 X

FOREIGN PATENT DOCUMENTS 0073301 3/1983 European Pat. Off. .

OTHER PUBLICATIONS van Straten et al., Volatile Compounds in Food, 4th Ed., 1977, Central Inst. for Nutrition & Food Research tno, Netherlands, pp. 75.1–75.2.
J. Am. Chem. Soc. 61, 1939, pp. 3303–3306.
Tetrahedron Letters, vol. 23, No. 3, 1982, pp. 335–338.

*Primary Examiner*—Joseph Golian
*Attorney, Agent, or Firm*—Sprung Horn Kramer & Woods

[57] ABSTRACT

A perfumed or edible composition comprising an appropriate carrier and an amount of 5-methyl-hept-2-en-4-one effective to impart its fragrance or flavor to the composition. It imparts a fragrance and flavor reminiscent of hazelnut.

3 Claims, No Drawings

FLAVORING WITH 5-METHYL-HEPT-2-EN-4-ONE

The invention relates to the use of 5-methyl-hept-2-en-4-one as a fragrance and/or flavor and to fragrance compositions and/or flavoring compositions containing this substance.

Within the framework of the investigation under which ketols can be obtained by partial hydrogenation of 1,3-diketones, 5-methyl-hept-2-en-4-one has been described as an intermediate in the preparation of the saturated ketone which was used for determination of the ketol structure (J. Am. Chem. Soc. 61, 3303 (1939)).

Tetrahedron Letters 23, 335 (1982) describes a reaction mixture which consists of 4 parts of 5-methyl-hept-1-en-4-one and 1 part of 5-methyl-hept-2-en-4-one.

No data on the properties of 5-methyl-hept-2-en-4-one are known.

It has been found that 5-methyl-hept-2-en-4-one may be used as a fragrance and/or flavor.

Moreover, fragrance compositions and/or flavoring compositions containing 5-methyl-hept-2-en-4-one have been found.

5-Methyl-hept-2-en-4-one, to be used according to the invention, is a valuable fragrance and/or flavor which is higher concentration has a nutty note, in particular a note reminiscent of hazelnut, in greater dilution exhibits an enhancer action and, in fragrance compositions, imparts greater naturalness, being usable in amounts of 0.01 to 10% by weight, based on the total composition.

5-Methyl-hept-2-en-4-one to be used according to the invention can be obtained for example by reacting 2-butyl-magnesium bromide (prepared, for example, from 2-bromo-butane and magnesium filings) with crotonaldehyde in ether solution. 5-Methyl-hept-2-en-4-ol is obtained as an intermediate and is oxidized with a mixture of sodium dichromate and sulphuric acid to give 5-methyl-hept-2-en-4-one. The 5-methyl-hept-2-en-4-one is obtained as a mixture of the cis- and trans-isomers, with the latter predominating. The isomer mixture can be separated into the cis-isomer and trans-isomer by simple methods of separation, such as, for example, fractional distillation by a packed column or slotted tube column or preparative gas chromatography. However, it has been found that the use of the individual isomers offers no advantages over the use of the mixture.

The fragrance to be used according to the invention is employed in combination with other fragrances, known per se (Arctander, Perfume and Flavor Chemicals, Montclair, N.J. (USA), 1969) and ethereal oils (Arctander, Perfume and Flavor Materials of Natural Origin., Elisabeth, N.J. (USA), 1960) and leads to perfume bases and fragrance compositions having highly expressive notes, which are outstandingly suitable for perfuming finished products in the aerosol, detergent and industrial chemicals sector, but especially for the fine perfumery or cosmetic sector, for example for detergents, hair conditioners, foam baths, bath salt, dishwasher detergents, washing powders, soaps, antiperspirants, powders, creams, shaving lotion, aftershave lotions, air fresheners, toilet cleaners, room sprays, antiperspirant sprays, deodorant sprays, body sprays, insecticide sprays and sun lotions.

The perfume compositions and perfumed products are prepared in a customary manner, for example by mixing the components.

Moreover, the 5-methyl-hept-2-en-4-one to be used according to the invention is a valuable flavor distinguished by a surprisingly low taste threshold. Thus, in 3% strength sucrose solution the perception threshold is at about $5 \times 10^{-6}$ ppm and the recognition threshold at about $30 \times 10^{-6}$ ppm.

At the perception threshold 5-methyl-hept-2-en-4-one produces a taste which can be described as "soft, buttery, full sensation in the mouth" while at and above the recognition threshold the description of the taste is "nutty, hazelnut, soft, buttery, full sensation in the mouth". In addition to its specific characterization in the hazelnut direction in appropriate flavoring compositions, it has, in all non-nut types of compositions, a particularly rounding effect, and provides more naturalness through its buttery soft basic fullness.

The flavoring compositions prepared using 5-methyl-hept-2-en-4-one can be employed in the entire foodstuff and beverage field, in mouth care and in animal feeds. In particular, they are suitable for icings, fruit pastilles, hard caramels, toffee compositions, chocolate compositions, nougat compositions, fat compositions, margarine, edible oil, cake flours, biscuit compositions, patisserie, extruded products, dairy products, sour milk products, drinks, ices, chewing gum, mouth-care agents, tobacco products, ready-cooked meals, meat and sausage products, soups, sauces, preserved vegetables, spirits, vegetable and microbial proteins and all types of industrially produced animal feeds.

The 5-methyl-hept-2-en-4-one according to the invention is employed in amounts of $5 \times 10^{-6}$ ppm to 100 ppm, preferably $3 \times 10^{-5}$ ppm to 10 ppm, based on the ready-to-consume foodstuff.

PREPARATION

Example 1

2-Butylmagnesium bromide is prepared from 24.32 g of magnesium filings and 137 g of 2-bromobutane in 100 ml of ether. 56 g of crotonaldehyde dissolved in 60 ml of ether are added dropwise to the solution at 0° to 10° C. The mixture is then boiled for 2 hours under reflux temperature. Thereafter it is cooled, the batch decomposed with ice water/hydrochloric acid and the product extracted, neutralized and distilled. 56 g of 5-methyl-hept-2-en-4-ol of boiling point 70° C./18 mb are obtained. To 52 g of this alcohol there is slowly added a mixture of 40.34 g of sodium dichromate and 54.1 g of sulphuric acid, while cooling with ice. After a further hour's reaction at room temperature, the batch is extracted with ether, the organic phase is washed until neutral, the solvent stripped off and the crude product distilled. Redistillation using a slotted tube column gives 17.2 g of 5-methyl-hept-2-en-4-one of boiling point 72° C./20 mb.

USE

Example 2

A perfume composition having an orange note is prepared by mixing the following components:

| | |
|---|---|
| white orange oil | 650 |
| linalyl acetate | 325 |
| styrolyl acetate | 20 |

| | |
|---|---|
| 95% strength nootkatone | 5 |
| | 1000 parts by weight |

On addition of 1 part by weight of 5-methyl-hept-2-en-4-one the composition acquires a very natural, mandarin-peel and orange-peel note.

Example 3

A flavoring composition A with apple flavor is prepared by mixing the following constituents:

| | |
|---|---|
| acetaldehyde | 10 |
| n-butyl acetate | 50 |
| trans-hex-2-enal | 30 |
| ethyl acetate | 30 |
| hexyl acetate | 20 |
| n-butyric acid | 10 |
| propylene glycol | 850 |
| | 1000 parts by weight |

A flavoring composition B is prepared by adding 0.002% of 5-methyl-hept-2-en-4-one to A.

A and B are added in a dose of 7.5 ppm to a solution of 5% of sucrose and 0.05% of citric acid in water and subjected to a flavor test. Composition B is unanimously preferred to composition A. The flavor of composition B is described as being fuller, more natural, juicier and more typical of ripe apples.

Example 4

A flavoring composition C with vanilla flavor is prepared by mixing the following constituents:

| | |
|---|---|
| vanillin | 50 |
| ethylvanillin | 10 |
| heliptropin | 2 |
| diacetyl | 2 |
| propylene glycol | 936 |
| | 1000 parts by weight |

A flavoring composition D is prepared by adding 0.004% of 5-methyl-hept-2-en-4-one to C.

C and D are added in a dose of 37.5 ppm to a solution of 5% of sucrose in water and subjected to a flavor test. Composition D is clearly preferred to composition C. The flavor of composition D is described as fuller, softer and more natural.

Example 5

A flavoring composition E with walnut flavor is prepared by mixing the following constituents:

| | |
|---|---|
| vanillin | 10 |
| methylcyclopentenolone | 30 |
| resorcinol dimethyl ether | 10 |
| maltol | 5 |
| propylene glycol | 945 |
| | 1000 parts by weight |

A flavoring composition F is prepared by adding 0.003% of 5-methyl-hept-2-en-4-one to E.

F and E are added in a dose of 75 ppm to a solution of 5% of sucrose in water and subjected to a flavor test. Composition F is clearly preferred to composition E. The flavor of composition F is described as fuller, softer and more typical of walnut.

Example 6

A flavoring composition G with hazelnut flavor is prepared by mixing the following constituents:

| | |
|---|---|
| vanillin | 30 |
| benzaldehyde | 10 |
| furfurol | 5 |
| 2-ethyl-3,5(3,6)-dimethylpyrazine | 5 |
| 2-methyl-3-ethyl-pyrazine | 5 |
| resorcinol dimethyl ether | 50 |
| propylene glycol | 895 |
| | 1000 parts by weight |

A flavoring composition H is prepared by adding 0.05% of 5-methyl-hept-2-en-4-one to G.

G and H in a dose of 15 ppm are added to a solution of 5% of sucrose in water and subjected to a flavor test. Composition H is clearly preferred to composition G. The flavor of composition H is described as fuller, more natural and substantially more typical of hazelnut.

Example 7

A flavoring composition I with mushroom flavor is prepared by mixing the following constituents:

| | |
|---|---|
| oct-1-en-3-ol | 40 |
| hexanol | 5 |
| propylene glycol | 955 |
| | 1000 parts by weight |

A flavoring composition J is prepared by adding 0.01% of 5-methyl-hept-2-en-4-one to I.

I and J are added in a dose of 7.5 ppm to a solution of 0.5% of sodium chloride in water and subjected to a flavor test. Composition J is clearly preferred to composition I. The flavor of composition J is described as fuller, substantially more natural and more typical in mushroom character.

It will be appreciated that the instant specification and examples are set forth by way of illustration and not limitation, and that various modifications and changes may be made without departing from the spirit and scope of the present invention.

What is claimed is:

1. An edible composition comprising a foodstuff and an amount of 5-methyl-hept-2-en-4-one effective to impart a nut flavor to the composition.

2. An edible composition according to claim 1, wherein the 5-methyl-hept-2-en-4-one is present in about $5 \times 10^{-6}$ to 100 ppm.

3. In the imparting of a nut flavor to the taste of a foodstuff, the improvement which comprises employing as the modifying agent an amount effective therefor of 5-methyl-hept-2-en-4-one.

* * * * *